United States Patent [19]

Rydell

[11] Patent Number: 5,047,027
[45] Date of Patent: Sep. 10, 1991

[54] TUMOR RESECTOR

[75] Inventor: Mark A. Rydell, Golden Valley, Minn.

[73] Assignee: Everest Medical Corporation, Minneapolis, Minn.

[21] Appl. No.: 511,776

[22] Filed: Apr. 20, 1990

[51] Int. Cl.⁵ .............................................. A61B 17/39
[52] U.S. Cl. ....................................... 606/48; 606/50
[58] Field of Search ............................ 606/46, 48, 50

[56] References Cited

U.S. PATENT DOCUMENTS 4,043,342  8/1977  Morrison, Jr. ..................... 606/50
4,060,087  11/1977  Hiltebrandt et al. ............. 606/48 X

FOREIGN PATENT DOCUMENTS 2501034  9/1982  France ............................. 606/50
782816  11/1980  U.S.S.R. .......................... 606/50

Primary Examiner—Lee S. Cohen
Attorney, Agent, or Firm—Haugen and Nikolai

[57] ABSTRACT

A bipolar electrosurgical instrument designed for resecting tumorous growths from the esophagus, bladder or other internal organ where the site of the tumor is reached by way of an endoscope, the instrument being dimensioned to fit down the central lumen of the endoscope, comprises an elongated, flexible tube having a conductive helical spring cantilevered from the distal end of the tube and forming a return electrode and a conductive wire hoop spaced a predetermined gap distance from the distalmost convolution of the helical spring and whose plane is perpendicular to the longitudinal axis of the flexible tube forms the active electrode. Wires for applying a high frequency RF voltage across the electrodes extend through the lumen of the flexible tube. As the distal end portion of the instrument is dragged over the tumor to be resected, the cantilevered helical spring is laterally displaced, allowing the RF current leaving the active hoop electrode to cut through the tumorous tissue.

9 Claims, 1 Drawing Sheet

TUMOR RESECTOR

BACKGROUND OF THE INVENTION

I. Field of the Invention

This invention relates generally to electrosurgical apparatus and more particularly to a bipolar electrosurgical instrument which may be routed through an endoscope or similar device such as a resectoscope, a laparoscope or videoscope, and especially adapted for resecting tumors and the like from body organs accessible through such a device.

II. Discussion of the Prior Art

Electrosurgery has become a widely adopted procedure for treating a wide variety of medical problems. This type of surgery offers the advantage of not only readily cutting tissue but also effecting hemostasis through cauterization. In monopolar electrosurgery, a high frequency RF generator has its outputs connected between a large area skin-contacting body electrode and the blade or wire used to effect cutting. The body electrode is remote from the active cutting electrode and currents flow through generally indeterminate paths back to the body electrode. In bipolar electrosurgery, the active or cutting electrode and the return electrode are generally closely spaced to one another such that the return currents are confined to the tissue positioned between the active electrode and the return electrode on the instrument. Generally speaking, then, improved control during the surgical procedure can be achieved using bipolar electrosurgical techniques.

The Morrison Pat. No. 4,043,342 describes a bipolar electrosurgical device in which the active electrode comprises a rigid, needle and the return electrode a rigid, inflexible cap through which the needle electrode passes in an insulating fashion. This device is primarily intended as a hand-held electrosurgical scalpel which does not lend itself to surgical procedures except those that can be reached through a body incision. It is oftentimes desirable to effect a surgical procedure in a location accessible through an existing body orifice. For example, patients suffering from esophageal cancer may develop tumors which grow to a size where they can effectively block the esophagus, preventing food from passing to the stomach. The blockage problem can oftentimes be resolved by resecting the tumor by an instrument which may be fitted through the lumen of an endoscope or videoscope whereby the physician can view the surgical site.

In yet another instance, bladder tumors may be resected by first passing a endoscope through the urethra and into the bladder. However, a suitable instrument is then needed to reach those locations within the bladder where the tumors may be present. Until now, there has not been an electrosurgical instrument that can effectively be used to resection tumors using an endoscope to gain access to the surgical site. The present invention provides such an instrument.

SUMMARY OF THE INVENTION with the present invention, the bipolar electrosurgical instrument comprises an elongated, small-diameter, flexible, plastic tube having a proximal end, a distal end and at least one lumen extending from the proximal end to the distal end. The return electrode comprises a conductive helical spring member secured to the exterior of the plastic tube and it is cantilevered distally beyond the distal end of the plastic tube. The active electrode consists of a conductive wire hoop having a stem portion integrally formed therewith which passes through the central opening of the helical spring and into the distal end portion of the plastic tube. The diameter of the hoop and that of the convolutions at the end of the helical return electrode are sufficiently small to pass through the lumen of an endoscope. First and second insulated wires pass through the lumen of the plastic tube and respectively join to the active and return electrodes. This permits RF energy from an electrosurgical generator to be impressed across the two electrodes.

Because of the flexible nature of the spring return electrode which is cantilevered from the distal end of the plastic tube, as the distal tip portion of the instrument is brushed across the tumorous tissue to be excised, it is displaced laterally thereby increasing the area of contact between the return electrode and tissue and enhancing the cutting properties of the active hoop electrode.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
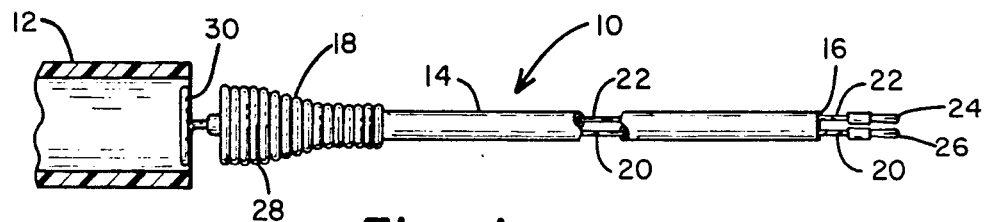
FIG. 1 is a side elevation of the electrosurgical instrument of the present invention.

Referring first to FIG. 1, there is indicated generally by numeral 10 an electrosurgical instrument especially designed for resecting tumors in locations assessable through a videoscope or an endoscope. A proximal end portion of such an endoscope is shown in cross-section and is identified by numeral 10. The instrument itself comprises an elongated, flexible plastic tube 14 having a proximal end 16 and a distal end 18. The tube 14 may have one or more lumens extending the full length thereof for allowing conductors 20 and 22 to pass therealong in insulated fashion from the proximal end 16 and beyond the distal end 18. To facilitate connecting the electrosurgical instrument 10 to an electrosurgical generator, the proximal ends of the wires 20 and 22 preferably will have a suitable connector, such as the banana plugs 24 and 26, for mating with female jacks on the generator. Affixed to the proximal end 18 of the tube 14 is a return electrode which, in accordance with the present invention, comprises a helically wound conductive wire 28 which is effectively cantilevered relative to the distal end 18 of the tube. As will be explained in greater detail when the cross-sectional view of FIG. 2 is discussed, one of the wires 24 or 26 passes through the wall of the tube 14 to connect with the return electrode 28.

Also fitted into the distal end of the elongated tube 14 is an assembly including an active electrode 30 which preferably has the form of a circular hoop whose plane extends perpendicular to the longitudinal axis of the tube 14. The active electrode 30 is spaced apart from and, therefore, insulated with respect to the return electrode 28. As can be seen in FIG. 1, the outside diameter of the active hoop electrode 30 is approximately the same as the most distal convulsion of the tapered, spiral wound return electrode 28 and both are of a size permitting them to pass through the lumen of the endoscope 12.

Figure 2:
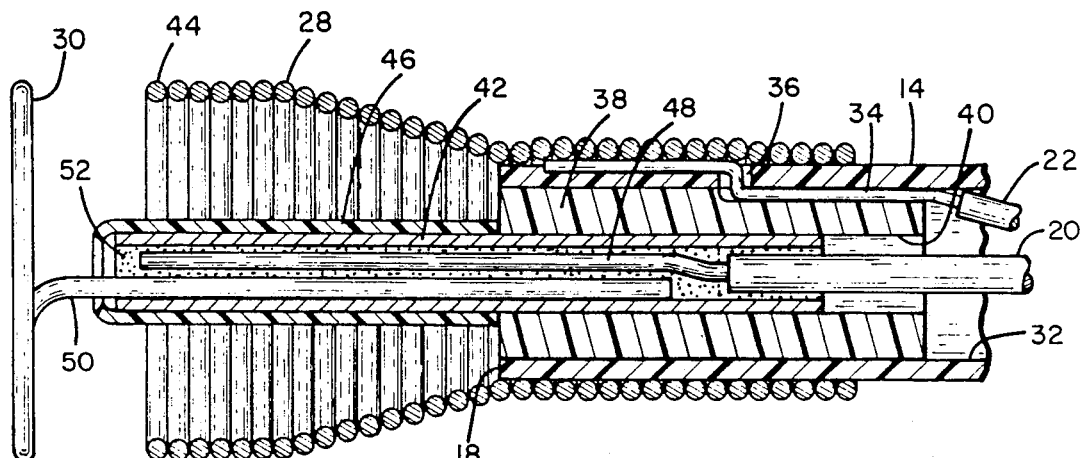
FIG. 2 is a greatly enlarged, cross-sectional view of the distal end portion of the electrosurgical instrument of FIG. 1.

Referring now to FIG. 2, there is illustrated a cross-sectional and greatly enlarged view of the distal end portion of the electrosurgical instrument 10 of FIG. 1. Assuming that only a single lumen 32 is provided in the elongated flexible plastic tubular member 14, the wire 22 will be insulated over substantially its entire length but with the insulation stripped free over a distal end portion thereof to expose the bare conductor segment 34. This bare conductor segment passes through an aperture 36 formed through the side wall of the tube 14 and then extends along the outer surface of the tube 14 for a predetermined distance. A tubular bushing 38, made from a suitable medical-grade plastic, such as polysulfone, is fitted into the lumen 32 of the tube 14 and provides a back-up allowing the helically wound wire forming the return electrode 28 to be wrapped tightly about the exterior of the tube 14, and thus providing intimate electrical contact between the helical electrode 28 and the exposed portion 34 of the conductor 20.

With continued reference to FIG. 2, it can be seen that there is fitted within the bore 40 of the tubular plastic bushing 38 a conductive metal tube, preferably formed from stainless steel and which is identified by numeral 42. The stainless steel tube 42 extends beyond the distal end 18 of the elongated flexible plastic tubular member 14 and beyond the distalmost convolution 44 of the helically wound wire return electrode 28. The portion of the conductive tube 42 extending beyond the distal end 18 of the plastic tube 14 is covered with a plastic insulating sheath 46. A Teflon heat shrink tube works well in this application.

The insulation on the wire 20 is stripped from the distal end portion thereof to expose the bare conductive segment 48. This segment extends toward but short of the distal end of the tube 42. Also fitted within the bore of the conductive tube 42 is a stem portion 50 which is formed integrally with the active hoop electrode 30 and which extends perpendicular to the plane of the hoop. The hoop electrode 30 is held in position by filling the voids remaining in the bore of the conductive tube 42 with a suitable conductive epoxy material 52 which becomes cured or hardened when exposed to heat above a predetermined temperature. Such an epoxy may comprise TRA-DUCT 2916 manufactured and sold by Tra-con Inc. As such, the bare wire 48 and the wire hoop 50 will be electrically joined to one another via a very low impedance path.

With no limitation intended, the overall length of the tube 14 may be 84 inches and may be approximately 0.095 inch in outer diameter and may have a wall thickness of approximately 0.01 inch. The portion of the spiral return electrode 28 extending beyond the distal end 18 of the tube 14 may be approximately 0.15 inch and taper, as shown, to an outside diameter at distal convolution 44 to a diameter of 0.15 inch. The gap between the convolution 44 and the hoop 30 may typically be about 0.05 inch.

The tube 14 is preferably (but not necessarily) a polyester blend sold under the trademark HYTREL by DuPont and may have a hardness of 72d or 82d.

Figure 3:
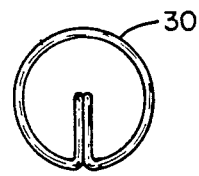
FIG. 3 is an end view of the active electrode portion of the electrosurgical instrument of FIG. 1.

FIG. 3 comprises an end view of the hoop 30 showing the manner in which the wire comprising the hoop is bent to create the integrally formed stem portion 50 thereof.

It is also contemplated that the bushing 38 and the sheath or sleeve 46 may be integrally molded from an appropriate plastic such as polysulfone and appropriately dimensioned to receive the conductive metal tube 42 in the bore thereof. That is to say, the bushing and sleeve would be made out of the same material in a molding operating making it unnecessary to provide a separate heat-shrink sleeve for the portion of the metal tube 42 extending beyond the distal end 18 of the tube 14.

Figure 4:
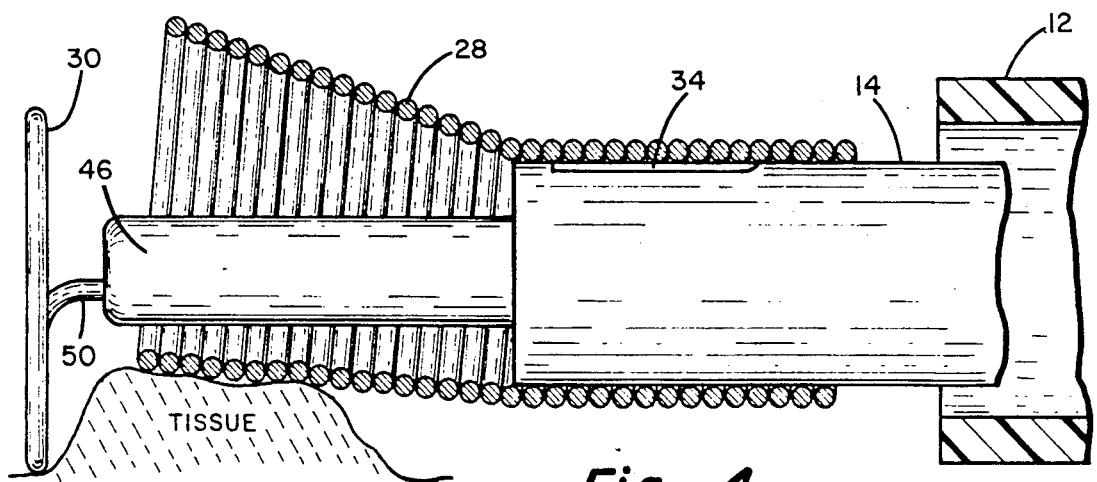
FIG. 4 is a greatly enlarged view of the distal end portion of the electrosurgical instrument of FIG. 1 when drawn against tissue to be resected.

In use, an endoscope or similar device may be placed through the appropriate body orifice for gaining access to the tissue to be excised and then the electrosurgical instrument of the present invention may be routed through the endoscope and into the organ where the tissue to be excised is located. As can best be seen in the view of FIG. 4, as the distal end portion of the instrument is pushed out the distal end of the endoscope 12 and encounters the tissue obstruction to be excised, the cantilevered portion of the return electrode 28 is deflected laterally and the hoop electrode 30, i.e., the active electrode, is positioned beyond the tumorous growth. Now, when the electrosurgical generator (not shown) coupled to the instrument 10 is activated to apply a high RF voltage between the electrodes 28 and 30 while the instrument is retracted back towards and into the endoscope, the tumorous tissue will be cut free from the organ comprising the host site while simultaneous coagulation of bleeding occurs. Given the amount of surface area in contact with the return electrode 28, cutting will tend to be limited to the tumorous tissue located between the hoop electrode 30 and the return electrode. Hence, the cutting is very well controlled. Because of the manner in which the return electrode is capable of deflecting to the side, the active electrode becomes more exposed to the tissue relative to the return electrode and can, therefore, cut larger amounts of tissue. Since the return electrode can deflect in any direction, the device can cut on any side presented to the tissue.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar electrosurgical instrument comprising:
   (a) an elongated, flexible plastic tube having a proximal end, a distal end and at least one lumen extending rom said proximal end to said distal end;
   (b) a first wire conductor having a proximal end and extending through said lumen of said plastic the from said proximal end of said tube and beyond said distal end of said tube;

(c) a second wire conductor having a proximal end extending through said lumen of said plastic tube in insulated relation to said first wire conductor;

(d) a first electrode including a conductive helical spring member having proximal and distal ends, the proximal end of said spring member being secured to the exterior of said plastic tube and extending distally beyond said distal end of said plastic tube;

(e) means for connecting said second wire conductor to said conductive helical spring member;

(f) a second electrode including a conductive wire hoop projecting distally beyond the distal end of said helical spring member to form a gap therebetween, the plane of said hoop being perpendicular to the longitudinal axis of said plastic tube; and (g) means for connecting said first wire conductor to said second electrode.

2. The bipolar electrosurgical instrument as in claim 1 and further including an aperture formed through said plastic tube near said distal end thereof, said second wire conductor passing through said aperture to connect to said helical spring member.

3. The bipolar electrosurgical instrument as in claim 1 wherein said for means for connecting sad first wire conductive to said second electrode comprises:

(a) a conductive metal tube fitted into said lumen of said plastic tube and projecting distally outward from said distal end to be surrounded by and out of contact with the convolutions of said helical spring member;

(b) a stem formed integrally with said hoop and projecting perpendicular to said plane of said hoop, said stem extending into the lumen of said metal tube along with the portion of said first wire which extends beyond said distal end of said plastic tube; and (c) a conductive material joining said portion of said first wire to said stem and to said metal tube.

4. The bipolar electrosurgical instrument as in claim 3 and further including an insulating sleeve surrounding said metal tube.

5. The bipolar electrosurgical instrument as in claim 4 wherein the portion of said helical spring member extending beyond said distal end of said plastic tube is laterally displaceable.

6. The bipolar electrosurgical instrument as in claim 3 and further including a tubular plastic bushing fitted into said lumen of said plastic tube and surrounding said metal tube.

7. The bipolar electrosurgical instrument as in claim 1 wherein the convolutions of said helical spring member have an increasing radius over a predetermined range extending between said distal end of said plastic tube and said distal end of said helical spring member.

8. The bipolar electrosurgical instrument as in claim 1 wherein the radius of said hoop is generally equal to the maximum radius of said helical spring member.

9. The bipolar electrosurgical instrument as in claim 1 and further including electrical terminals connected to said proximal ends of said first and second wire conductors.

* * * * *

UNITED STATES PATENT AND TRADEMARK OFFICE
CERTIFICATE OF CORRECTION

PATENT NO. : 5,047,027
DATED : September 10, 1991
INVENTOR(S) : Mark A. Rydell

It is certified that error appears in the above-identified patent and that said Letters Patent is hereby corrected as shown below:

Col. 4, line 66, Claim 1, delete "rom" and put instead -- from --.

Col. 4, line 68, Claim 1, delete "the" and put instead -- tube --.

Col. 5, line 26, Claim 3, delete "for" (first occurrence).

Col. 5, line 26, Claim 3, delete "sad" and put instead -- said --.

Col. 5, line 27, Claim 3, delete "conductive" and put instead -- conductor --.

Signed and Sealed this

Ninth Day of February, 1993

Attest:

STEPHEN G. KUNIN

*Attesting Officer*          *Acting Commissioner of Patents and Trademarks*